United States Patent
Biava et al.

(10) Patent No.: US 8,304,410 B2
(45) Date of Patent: Nov. 6, 2012

(54) PYRROLE COMPOUNDS AS INHIBITORS OF MYCOBACTERIA, SYNTHESIS THEREOF AND INTERMEDIATES THERETO

(75) Inventors: Mariangela Biava, Rome (IT); Giulio Cesare Porretta, Rome (IT); Raffaello Pompei, Rome (IT); Maurizio Botta, Siena (IT); Fabrizio Manetti, Siena (IT); Alessandro De Logu, Siena (IT)

(73) Assignees: Università degli Studi di Roma "La Sapienza", Rome (IT); Università degli Studi di Siena, Siena (IT)

( * ) Notice: Subject to any disclaimer, the term of this patent is extended or adjusted under 35 U.S.C. 154(b) by 206 days.

(21) Appl. No.: 12/679,848

(22) PCT Filed: Sep. 25, 2008

(86) PCT No.: PCT/IB2008/053905
§ 371 (c)(1),
(2), (4) Date: Mar. 24, 2010

(87) PCT Pub. No.: WO2009/040755
PCT Pub. Date: Apr. 2, 2009

(65) Prior Publication Data
US 2010/0197672 A1    Aug. 5, 2010

(30) Foreign Application Priority Data
Sep. 26, 2007    (EP) ..................... 07117243

(51) Int. Cl.
C07D 207/33    (2006.01)
C07D 417/06    (2006.01)
A61K 31/402    (2006.01)

(52) U.S. Cl. ............. 514/227.8; 514/254.01; 514/235.5; 514/326; 544/60; 544/372; 544/141; 546/208; 548/314.7

(58) Field of Classification Search ............... 514/227.8, 514/254.01, 235.5, 326; 544/60, 372, 141; 546/208; 548/314.7
See application file for complete search history.

(56) References Cited

FOREIGN PATENT DOCUMENTS
WO    2006/092822 A    9/2006

OTHER PUBLICATIONS

Biava, et al., "Antimycobacterial compounds. Optimization of the BM 212 structure, the lead compound for a new pyrrole derivative class", Bioorganic & Medicinal Chemistry, 13(4):1221-1230, 2005.
Khanna, et al., "1,2-Diarylpyrroles as potent and selective inhibitors of cyclooxygenase-2", Journal of Medicinal Chemistry, 40(11):1619-1633, 1997.

*Primary Examiner* — Kahsay T Habte
(74) *Attorney, Agent, or Firm* — Lucas & Mercanti, LLP

(57) ABSTRACT

The present invention relates to compounds having formula 3

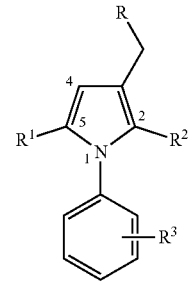

as well as the synthesis, intermediates and methods of using the same.

5 Claims, No Drawings

PYRROLE COMPOUNDS AS INHIBITORS OF MYCOBACTERIA, SYNTHESIS THEREOF AND INTERMEDIATES THERETO

CROSS-REFERENCE TO RELATED APPLICATIONS

This application is a 371 of PCT/IB2008/053905 filed Sep. 25, 2008, which claims the benefit of European Application No. 07117243.1 filed Sep. 26, 2007, the contents of each of which are incorporated herein by reference.

FIELD OF THE INVENTION

The present invention concerns novel pyrrole compounds, derivatives of 1-{[1,5-bis(4-chlorophenyl)-2-methyl-1H-pyrrol-3-yl]methyl}-4-methylpiperazine (BM212). The invention concerns the use of the described compounds as antitubercular agents and a process to obtain intermediates and final compounds. The compounds of the invention are found to be more active and much less toxic than previously known compounds.

STATE OF THE ART

Tuberculosis (TB) is an infectious disease caused by *Mycobacterium tuberculosis* (MTB) responsible for a high death-rate in both industrialized and developing countries. According to a recent report compiled by the World Health Organisation (WHO), TB caused about 1.7 millions death in 2004 and the total number of new cases of TB has risen to 9 millions worldwide (Duncan et al., 2004; WHO, 2006). This is particularly alarming considering that these cases represent only 32% of the actual incidence.

The recent recrudescence of TB, along with *M. avium* infection, has been related with the spread of HIV infection. It is unclear if the rise in TB is due to new primary infection or to the reactivation of latent infection. However, infection in HIV-infected individuals has prompted a vigorous search for new drugs for the treatment of the disease. In fact, the progressive immunological deterioration associated with AIDS is often accompanied by opportunistic infections causing TB (*M. tuberculosis*) and non-TB (*M. avium*) mycobacterial diseases, as well as mycotic infections caused by *Candida albicans* and *Cryptococcus neoformans*. Treatment of these infections, along with other opportunistic infections which cause the majority of all AIDS-related deaths, is often complicated by patient's intolerance to the drugs employed or pathogen's resistance to conventional drug therapy.

Drugs currently used to treat TB are Isoniazid (INH), Rifampicin (RIF), Pyrazinamide (PZA), Ethambutol (EMB), Streptomycin (SM), Cycloserin and para-aminosalicylic acid (PAS). For most of them, their mechanism of action is known. Indeed, INH and EMB inhibit mycolic acid biosynthesis, a fundamental component of the mycobacterial cell wall, acting at different steps of its synthesis. RIF inhibits pathogen's mRNA synthesis by binding to the β subunits of the DNA-dependent bacterial RNA polymerase. SM inhibits bacterial protein synthesis by interfering with molecular structures of the ribosomal 30S subunit. Cycloserin inhibits alanine racemase, which converts L-alanine to D-alanine, thus preventing its incorporation into the pentapeptide peptidoglycan of the bacterial cell wall. Finally, PAS is an antagonist of folates synthesis.

Recent studies demonstrated that nearly 19% of TB isolates from a hospital were resistant to INH and RIF, the two most common anti-tubercular agents. In general, resistance to INH and SM is more common than resistance to RIF, EMB and PZA.

As an empiric treatment of all MTB infections, even if drug resistance is not suspected, the four-drug regimen of INH, RIF, PZA, and EMB (or SM) is prescribed, until susceptibility results become available. Duration of therapy should be at least one year. However, very often this kind of therapy causes intolerance in patients. For this reason, the search for new drugs is necessary and the strategy followed has been to test known antibacterial drugs as antimycobacterial compounds. As a consequence, fluoroquinolones, oxazolidinones, β-lactams and macrolides are the newer drugs introduced in the therapy of antimycobacterial infections. Unfortunately, though these drugs revealed to be active, all of them rapidly induce resistance upon a prolonged treatment. Thus, they must always be used in conjunction with at least another anti-tubercular drug to which mycobacteria are susceptible.

Fluoroquinolones demonstrated in vitro and in vivo activity against MTB and they are also able to penetrate human macrophages in which mycobacteria live in their latent state. As an example, Levofloxacin is characterized by very favorable pharmacokinetic properties. However, new fluoroquinolones have been studied such as Sitafloxacin, Gatifloxacin and Moxifloxacin, all of them being more active than those already employed in therapy. In any case, quinolones are used in association with other drugs because they can induce resistance.

Moreover, many efforts have been made to broaden the activity of oxazolidinones (i.e., antibacterial effects) to mycobacteria.

Among β-Lactams, Amoxicillin-Clavulanate (amoxicillin-clavulanic acid association) is used as additive therapy for multi-drug resistant (MDR)-TB, demonstrating a favorable response in patient.

Macrolides as Claritromycin, Azithromycin and, more recently, Rifapentine revealed to be less active in vitro against MTB than fluoroquinolones. In general, they are used in combination with at least another drug in order to prevent resistance.

In this context, the search for new effective compounds endowed with a different mode of action seemed a possible solution to the above-mentioned intolerance and drug-resistance problems. Moreover, since in immuno-compromized patients, tubercular pathology is very often accompanied by mycotic infections caused by *Candida albicans, Candida* sp. and *Cryptococcus neoformans*, this concomitance has lead to search for new substances able to act both as antifungal and antimycobacterial.

The authors of the present invention have already synthesized anti-tubercular compounds with general structure 1 (Deidda et al., 1998, Biava et al., 1999, Biava et al., 1999b).

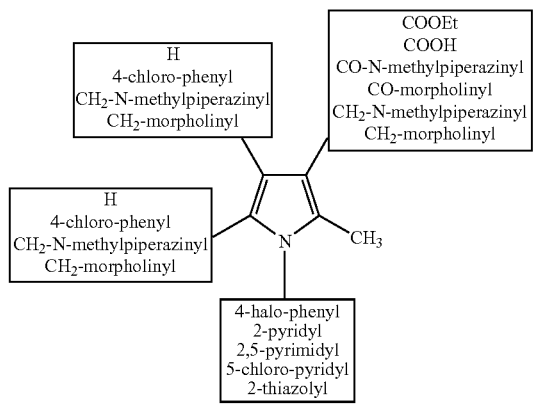

1

In particular, among them, the compound having the formula shown below, BM212, was identified as the most active, showing a potent and selective antifungal and antimycobacterial activity (Biava et al., 2003).

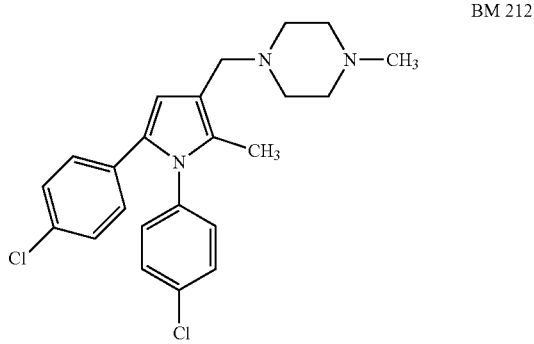

BM 212

More recently, other compounds have been synthesized by the authors, having the general structure 2 (Biava et al., 2004; Biava et al., 2005; Biava et al., 2006).

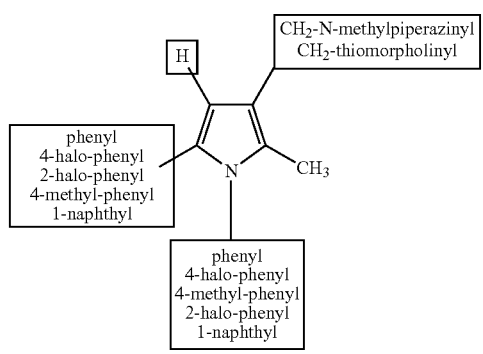

2

These compounds showed an anti-tubercular activity against both MTB and other atypical mycobacteria.

The international patent application WO 2004/026828 discloses BM212 derivatives having an activity against *M. tuberculosis* 27294 of between 0.125 and 16 μg/ml. Such compounds are also active against resistant clinical isolates. However, the toxicity of these compounds has not been assessed.

The international patent application WO 2006/092822 also describes BM212 derivatives having an activity against *M. tubeculosis* 103471 of between 0.5 and 16 μg/ml. Such compounds are also active against INH and RMP-resistant *M. tuberculosis*. These compounds possess a protection index (PI, defined as the ratio between cytotoxic concentration $CC_{50}$ and inhibitory concentration, MIC) between 0.5 and 160.

The international patent application WO 2005/020990 proposes pyrrol derivatives compounds having tuberculostatic activity, the structure of such compounds include a thiazolidine heterocycle:

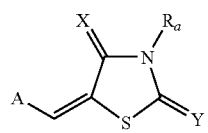

The instant invention refers to compounds found to be active toward different species of mycobacteria, including species that are responsible for tubercular diseases in general (namely, MTB) and for tubercular diseases in HIV-positive patients (namely, *M. avium*).

The compounds of the invention are also active against *M. tuberculosis* H37Rv and different species of mycobacteria resistant to INH and RIF.

Moreover, the authors of the instant invention present data on cytotoxic concentration ($CC_{50}$) and protection index (PI), which allow determining the effectiveness and safety of the compounds as anti-tubercular agents. As a matter of fact, the best compounds are characterized by a high activity and a low cytotoxicity. Compounds having this biological profile are effective antimycobacterial drugs, which can also act toward relevant species of atypical mycobacteria, such as *M. avium*.

In particular, the compounds of the present invention are more potent, less toxic and thus more selective than the compounds described in Biava et al., 2005 and Biava et al., 2006.

SUMMARY OF THE INVENTION

The present invention provides compounds endowed with a high activity toward Mycobacteria and a low cytotoxicity, i.e. compounds with a very good Protection Index (PI, defined as the ratio between cytotoxic concentration $CC_{50}$ and inhibitory concentration MIC). The compounds of the invention are also active against Mycobacteria resistant to INH and RIF. This is particularly relevant in view of the fact that antimycobacterial drugs are very often administered to immunocompromised patients for which drug toxicity is the effective cause of death.

The derivatives of the present invention possess excellent antimycobacterial activity. Moreover, they are
1. more active than existing drugs
2. less toxic than existing drugs
3. very active against dormient mycobacteria
4. very active against resistant mycobacteria It is therefore an object of the present invention a compound having the general formula 3

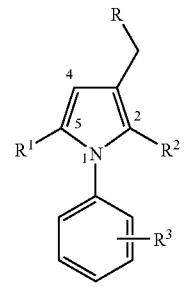

3 wherein:
R represents a morpholinyl, thiomorpholinyl, oxane, thioxane, N-methylpiperazinyl, N-isopropylpiperazinyl, N-acetylpiperazinyl, piperidyl or imidazolyl group;

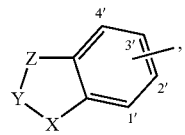

$R^1$ is
when Z is not present, $R^1$ is a substituted phenyl ring selected from: a o-, p- or m-methylsulfanyl phenyl, (Y=methyl, X=S), a o-, p- or m-ethylsulfanyl phenyl (Y=ethyl, X=S), a o-, p- or m-propylsulfanyl phenyl (Y=propyl, X=S), a o-, p- or m-isopropylsulfanyl phenyl (Y=isopropyl, X=S), a o-, p- or m-butylsulfanyl phenyl (Y=butyl, X=S), a o-, p- or m-isobutylsulfanyl phenyl (Y=isobutyl, X=S), a o-, p- or m-cyclopentylsulfanyl phenyl (Y=cyclopentylsulfanyl, X=S), a o-, p- or m-cyclohexylsulfanyl phenyl (Y=cyclohexyl, X=S), a o-, p- or m-methylsulfinyl phenyl (Y=methyl, X=SO), a o-, p- or m-methylsulfonyl phenyl (Y=methyl, X=SO$_2$), a o-, p- or m-sulfamoyl phenyl (Y=NH$_2$, X=SO$_2$), a o-, p- or m-methylsulfamoyl phenyl (Y=NHCH$_3$, X=SO$_2$) or a o-, p- or m-dimethylsulfamoyl phenyl (Y=N(CH$_3$)$_2$, X=SO$_2$) group;

R$^1$ is also a fused 5-6 heterocyclic ring represented by a benzo[b]thiophene (X=S, Y=Z=CH), benzo[c]thiophene (Y=S, X=Z=CH), benzo-1,2-thiazole (X=S, Y=N, Z=CH), and benzo-1,3-thiazole (X=S, Y=CH, Z=N) wherein the benzo[b]thiophene, the benzo-1,2-thiazole, and the benzo-1,3-thiazole can be bound to the C5 of the pyrrole ring through the carbon atom C1', C2', C3', or C4' and the benzo[c]thiophene can be bound to the C5 of the pyrrole ring through the carbon atom C1' or C2';

R$^2$ is H, methyl, ethyl, isopropyl, benzyl, o-chlorobenzyl, m-chlorobenzyl, p-chlorobenzyl, o-fluorobenzyl, m-fluorobenzyl, p-fluorobenzyl, o-methylbenzyl, m-methylbenzyl, p-methylbenzyl, o-trifluorobenzyl, m-trifluorobenzyl, p-trifluorobenzyl, o-methoxybenzyl, m-methoxybenzyl or p-methoxybenzyl;

R$^3$ is o-methyl, m-methyl, p-methyl, o-ethyl, m-ethyl, p-ethyl, o-propyl, m-propyl, p-propyl, o-isopropyl, m-isopropyl, p-isopropyl, o-methoxy, m-methoxy, p-methoxy, o-trifluoromethyl, m-trifluoromethyl, p-trifluoromethyl, o-chloro, m-chloro, p-chloro, o,o-dichloro, m,m-dichloro, o,p-dichloro, o-fluoro, m-fluoro, p-fluoro, o,o-difluoro, m,m-difluoro, o,p-difluoro, 1-naphthyl, o-methylsulfanyl, m-methylsulfanyl, p-methylsulfanyl, o-ethylsulfanyl, m-ethylsulfanyl, p-ethylsulfanyl, o-propylsulfanyl, m-propylsulfanyl, p-propylsulfanyl, o-isopropylsulfanyl, m-isopropylsulfanyl, p-isopropylsulfanyl, o-butylsulfanyl, m-butylsulfanyl, p-butylsulfanyl, o-isobutylsulfanyl, m-isobutylsulfanyl, p-isobutylsulfanyl, o-cyclopentylsulfanyl, m-cyclopentylsulfanyl, p-cyclopentylsulfanyl, o-cyclohexylsulfanyl, m-cyclohexylsulfanyl, p-cyclohexylsulfanyl, o-SOMe, m-SOMe, p-SOMe, o-SO$_2$Me, m-SO$_2$Me, p-SO$_2$Me, o-SO$_2$NH$_2$, m-SO$_2$NH$_2$, p-SO$_2$NH$_2$, o-SO$_2$NHMe, m-SO$_2$NHMe, p-SO$_2$NHMe, o-SO$_2$NMe$_2$, m-SO$_2$NMe$_2$ or p-SO$_2$NMe$_2$.

A preferred compound is N-(4-fluorophenyl)-2-methyl-3-thiomorpholinomethyl-5-(4-methylsulfanylphenyl)pyrrole (3a):

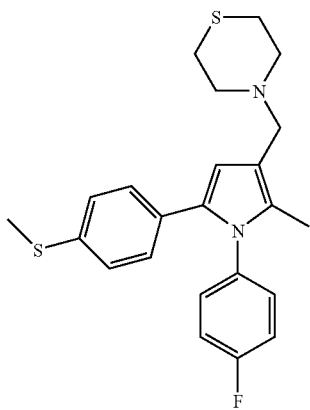

It is an object of the invention a compound of the invention for medical use. Preferably as an anti-tubercular agent.

A further object of the invention is the use of the compound of the invention for the preparation of a medicament endowed with anti-tubercular activity.

It is another object of the invention a pharmaceutical composition comprising the compound of the invention and appropriate excipients and diluents.

Preferably the pharmaceutical composition further comprises at least another compound endowed with antitubercular activity.

It is another object of the invention a process for the preparation of a compound of the invention comprising the following steps:

a) reaction of methyl vinyl ketone with the suitable aryl aldehyde having the following formula 5

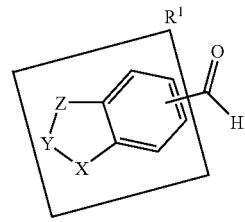

wherein R$^1$ is defined as above;

in the presence of 3-ethyl-5-(2-hydroxyethyl)-4-methylthiazolium bromide and triethylamine under conditions such as to obtain the appropriate intermediate 4

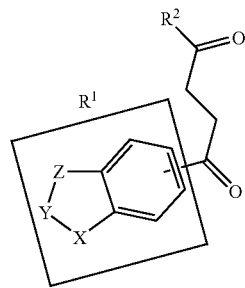

wherein R$^1$ and R$^2$ are defined as above;

b) extract and/or purify compound 4 as obtained under a);

c) allow to react compound 4 with appropriate aniline 7

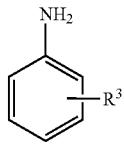

wherein R$^3$ is defined as above;

under conditions suitable for obtaining the appropriate intermediate 6;

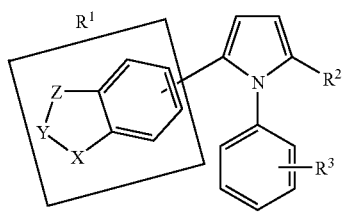

wherein R$^1$, R$^2$ and R$^3$ are defined as above;

d) purify compound 6 as obtained under c);
e) allow the appropriate amine (morpholine, thiomorpholine, N-methyilpiperazine, N-acetylpiperazine, N-isopropylpiperazine, piperidine, imidazole) to react with formaldehyde adding compound 6 under conditions suitable for obtaining the appropriate compound 3;
f) extract and/or purify product 3 as obtained under e).

It is an object of the invention an intermediate having formula 4:

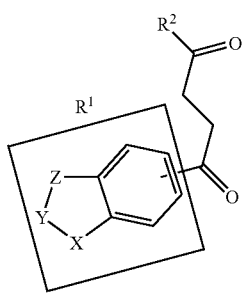

wherein $R^1$ and $R^2$ are defined as above.

It is a further object of the invention an intermediate having formula 6:

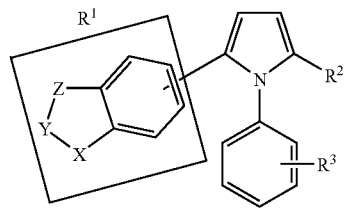

wherein $R^1$, $R^3$ and $R^2$ are defined as above.

The invention will now be described by means of non limiting examples.

EXAMPLES

Structure and Synthesis of Compound Having Formula 3

The procedure for the synthesis of compounds having structure 3 is the following:

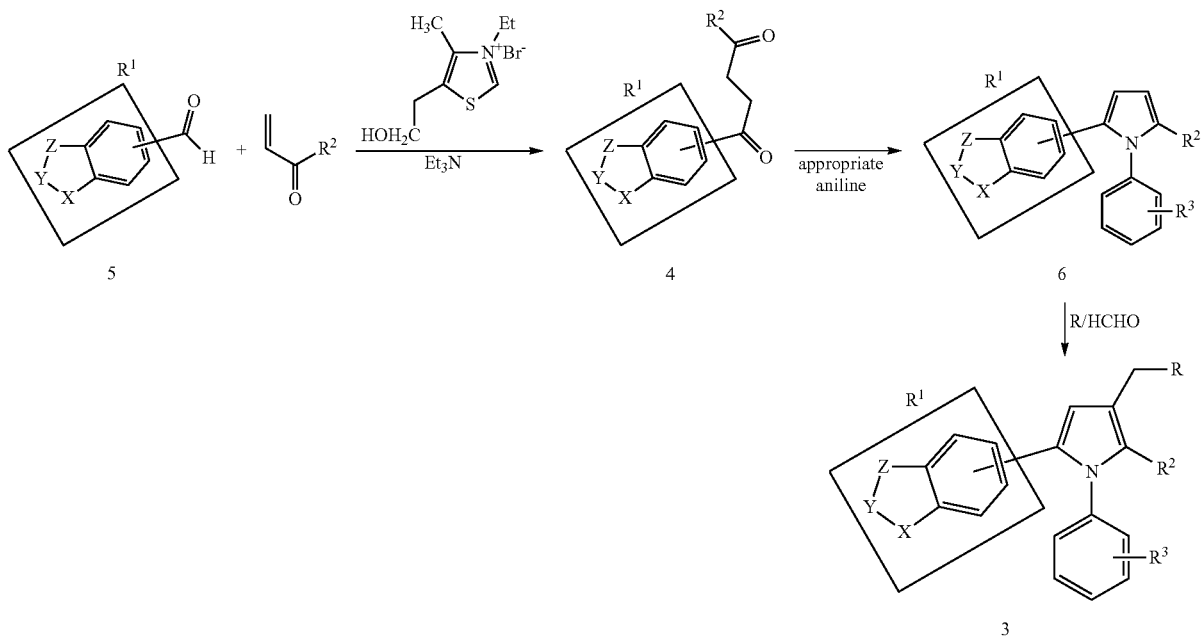

1) Preparation of Compounds Having Formula 4:

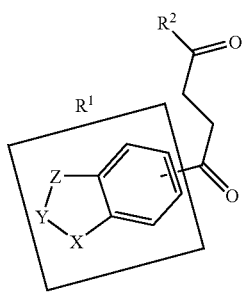

wherein $R^1$ is

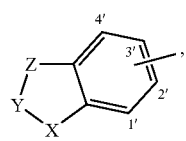

when Z is not present, $R^1$ is a substituted phenyl ring selected from: a o-, p- or m-methylsulfanyl phenyl, (Y=methyl, X=S), a o-, p- or m-ethylsulfanyl phenyl (Y=ethyl, X=S), a o-, p- or m-propylsulfanyl phenyl (Y=propyl, X=S), a o-, p- or m-isopropylsulfanyl phenyl (Y=isopropyl, X=S), a o-, p- or m-butylsulfanyl phenyl (Y=butyl, X=S), a o-, p- or m-isobutylsulfanyl phenyl (Y=isobutyl, X=S), a o-, p- or m-cyclopentylsulfanyl phenyl (Y=cyclopentylsulfanyl, X=S), a o-, p- or m-cyclohexylsulfanyl phenyl (Y=cyclohexyl, X=S), a o-, p- or m-methylsulfinyl phenyl (Y=methyl, X=SO), a o-, p- or m-methylsulfonyl phenyl (Y=methyl, X=$SO_2$), a o-, p- or m-sulfamoyl phenyl (Y=$NH_2$, X=$SO_2$), a o-, p- or m-methylsulfamoyl phenyl (Y=$NHCH_3$, X=$SO_2$) or a o-, p- or m-dimethylsulfamoyl phenyl (Y=$N(CH_3)_2$, X=$SO_2$) group;

$R^1$ is also a fused 5-6 heterocyclic ring represented by a benzo[b]thiophene (X=S, Y=Z=CH), benzo[c]thiophene (Y=S, X=Z=CH), benzo-1,2-thiazole (X=S, Y=N, Z=CH), and benzo-1,3-thiazole (X=S, Y=CH, Z=N) wherein the benzo[b]thiophene, the benzo-1,2-thiazole, and the benzo-1,3-thiazole can be bound to the C5 of the pyrrole ring through the carbon atom C1', C2', C3', or C4' and the benzo[c]thiophene can be bound to the C5 of the pyrrole ring through the carbon atom C1' or C2';

$R^2$ is H, methyl, ethyl, isopropyl, benzyl, o-chlorobenzyl, m-chlorobenzyl, p-chlorobenzyl, o-fluorobenzyl, m-fluorobenzyl, p-fluorobenzyl, o-methylbenzyl, m-methylbenzyl, p-methylbenzyl, o-trifluorobenzyl, m-trifluorobenzyl, p-trifluorobenzyl, o-methoxybenzyl, m-methoxybenzyl or p-methoxybenzyl;

a) Methyl vinyl ketone (0.016 mol) was reacted, in the presence of 3-ethyl-5-(2-hydroxyethyl)-4-methylthiazolium bromide (0.0032 mol) and triethylamine (0.011 mol), with the appropriate aryl aldehyde (0.016 mol) having the following formula 5:

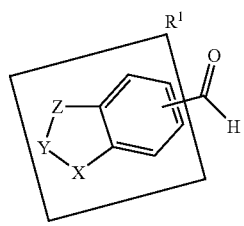

5 wherein $R^1$ is defined as above;
b) the mixture was stirred at 75° C. under a nitrogen atmosphere for 5 h or 23 h, depending on the particular substrate;
c) after cooling, treat the mixture with aqueous HCl until pH 2;
d) keep the mixture under stirring for 30 min;
e) extract the mixture with ethyl acetate and neutralize the aqueous phase with a $NaHCO_3$ solution;
f) purify the product by column chromatography on aluminium oxide (Brockmann grade II-III), eluting with benzene.

2) Preparation of Compounds Having Formula 6:

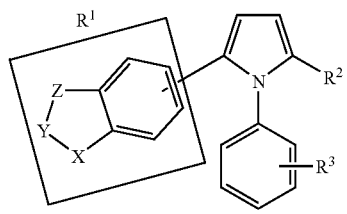

6 wherein $R^1$ and $R^2$ are defined as above and $R^3$ is o-methyl, m-methyl, p-methyl, o-ethyl, m-ethyl, p-ethyl, o-propyl, m-propyl, p-propyl, o-isopropyl, m-isopropyl, p-isopropyl, o-methoxy, m-methoxy, p-methoxy, o-trifluoromethyl, m-trifluoromethyl, p-trifluoromethyl, o-chloro, m-chloro, p-chloro, o,o-dichloro, m,m-dichloro, o,p-dichloro, o-fluoro, m-fluoro, p-fluoro, o,o-difluoro, m,m-difluoro, o,p-difluoro, 1-naphthyl, o-methylsulfanyl, m-methylsulfanyl, p-methylsulfanyl, o-ethylsulfanyl, m-ethylsulfanyl, p-ethylsulfanyl, o-propylsulfanyl, m-propylsulfanyl, p-propylsulfanyl, o-isopropylsulfanyl, m-isopropylsulfanyl, p-isopropylsulfanyl, o-butylsulfanyl, m-butylsulfanyl, p-butylsulfanyl, o-isobutylsulfanyl, m-isobutylsulfanyl, p-isobutylsulfanyl, o-cyclopentylsulfanyl, m-cyclopentylsulfanyl, p-cyclopentylsulfanyl, o-cyclohexylsulfanyl, m-cyclohexylsulfanyl, p-cyclohexylsulfanyl, o-SOMe, m-SOMe, p-SOMe, o-$SO_2$Me, m-$SO_2$Me, p-$SO_2$Me, o-$SO_2NH_2$, m-$SO_2NH_2$, p-$SO_2NH_2$, o-$SO_2$NHMe, m-$SO_2$NHMe, p-$SO_2$NHMe, o-$SO_2NMe_2$, m-$SO_2NMe_2$ or p-$SO_2NMe_2$.

a) the appropriate compound 4 was reacted with an equimolar amount of appropriate aniline 7

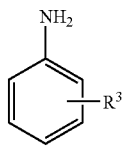

7 wherein $R^3$ is defined as above;
b) the mixture was heated at 100° C. for 3 h;
c) the obtained products were purified by column chromatography on aluminium oxide (Brockmann grade II-III), eluting with cyclohexane.

3) Preparation of the Compounds Having General Formula 3:

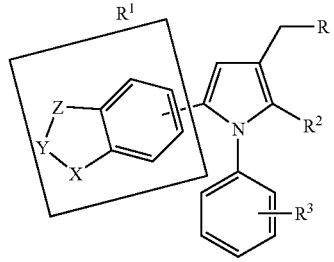

3 wherein R represents a morpholinyl, thiomorpholinyl, oxane, thioxane, N-methylpiperazinyl, N-isopropylpiperazinyl, N-acetylpiperazinyl, piperidyl or imidazolyl group;
$R^1$, $R^2$ and $R^3$ are defined as above;
a) allow to react 0.6 mol of a suitable amine with 0.6 mol of 36.5% (w/w) aqueous formaldehyde using 5 mL of glacial acetic acid as solvent;
b) using a dropping funnel, add the appropriate compound 6 (0.6 mol), dissolved in 1:2 acetic acid/acetonitrile mixture, dropwise to the Mannich adduct;
c) stir the mixture for 12 h at 25° C.;
d) neutralize the mixture with 30 mL of 20% (w/v) aqueous NaOH;
e) extract the solution with ethyl acetate and wash the organic phase with water to neutrality;
f) purify the so obtained product by column chromatography on aluminium oxide (Brockmann grade II-III), eluting the derivatives containing the N-methylpiperazine moiety with chloroform and those containing the thiomorpholine moiety with benzene.

Melting points were determined with a Fisher-Jones apparatus and are uncorrected. Elemental analyses are within ±0.4% of theoretical values.

As an example, the preparation of compound 3a starting from 4a:

1) Preparation of Compound 4a

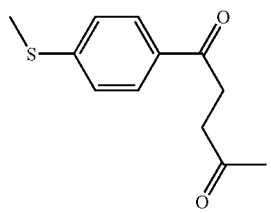

4a a) Methyl vinyl ketone (1.16 g, 0.016 mol) and p-methylsulfanylbenzaldehyde (2.4 g, 0.016 mol) were reacted in the presence of 3-ethyl-5-(2-hydroxyethyl)-4-methylthiazolium bromide (0.837 g, 0.0032 mol) and triethylamine (1.14 g, 0.011 mol).
b) Stir the reaction mixture at 75° C. under a nitrogen atmosphere for 24 h.
c) Cool the mixture to room temperature, add ice and 30 mL of concentrated HCl to the mixture until pH 2.
d) Stir for 30 min.
e) Extract with ethyl acetate and neutralize the combined organic fractions with an aqueous solution of $NaHCO_3$.
f) Dry the organic fraction on anhydrous sodium sulphate for 3 h.
g) Purify the product by column chromatography on aluminium oxide (Brockmann grade II-III), eluting with a 3:1 cyclohexane/ethyl acetate mixture (53% yield).

1') Alternative Method of Preparation of Compound having Formula 4a

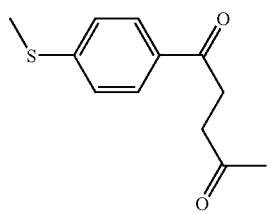

4a a) Methyl vinyl ketone (1.16 g, 0.016 mol) and p-methylsulfanylbenzaldehyde (2.4 g, 0.016 mol) were reacted in the presence of 3-ethyl-5-(2-hydroxyethyl)-4-methylthiazolium bromide (0.837 g, 0.0032 mol) and triethylamine (1.14 g, 0.011 mol);
b) put the mixture into a round-bottom flask equipped with a stir bar. Insert the flask into the cavity of the Discovery Microwave System apparatus and heat (150 W, for 15 min, internal temperature 70° C. and internal pressure 60 psi);
c) after cooling, treat the mixture with aqueous HCl until pH 2;
d) keep the mixture under stirring for 30 min;
e) extract the mixture with ethyl acetate and neutralize the aqueous phase with a $NaHCO_3$ solution;
f) dry the organic fraction over $Na_2SO_4$;
g) filter and concentrate in vacuo the crude product;
h) purify the product by column chromatography on aluminium oxide (Brockmann grade II-III), eluting with a mixture of cyclohexane:ethyl acetate, 3:1 v/v as eluant, re-crystallize from cyclohexane.

TABLE 1

Physicochemical properties of compound 4a.

| Compd | Mp, ° C. | Yield, % | Formula (MW) |
|---|---|---|---|
| 4a | 65 | 55 | $C_{12}H_{14}SO_2$ (222.30) |

2) Preparation of Compound 6a

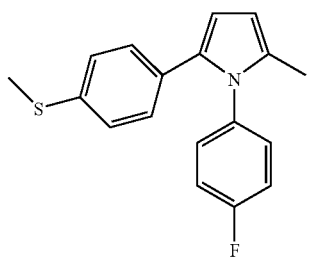

6a a) Compound 4a (1.55 g, 0.007 mol) was reacted at 100° C. for 3 h with p-F-aniline (0.78 g, 0.007 mol) and p-toluenesulphonic acid (0.08 g, 0.0005 mol).
b) Purify the obtained product by column chromatography on aluminium oxide (Brockmann grade II-III), eluting with cyclohexane (75% yield).

TABLE 2

Physicochemical properties of compound 6a.

| Compd | Mp, ° C. | Yield, % | Formula (MW) |
|---|---|---|---|
| 6a | 123 | 93 | $C_{18}H_{16}NFS$ (297.39) |

2') Preparation of Compounds 6b-6e

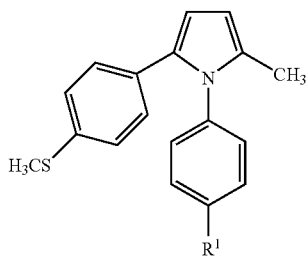

6b-e wherein
$R^1$ is methyl, ethyl, propyl, i-propyl.
a) the diketone 4a (0.62 g, 0.0028 mol) was dissolved in ethanol (2 mL) into a round-bottom flask equipped with a stir bar, the appropriate aniline (0.0028 mol) and p-toluen solfonic acid (0.027 g, 0.00017 mol) were added;
b) insert the flask into the cavity of the Discovery Microwave System apparatus and heat (150 W, for 30 min, internal temperature 160° C. and internal pressure 150 psi);
c) cool the reaction mixture and concentrate in vacuo;
d) purify the obtained product by column chromatography on aluminium oxide (Brockmann grade II-III), eluting with cyclohexane.

TABLE 2'

Physicochemical properties of compound 6b-e.

| Compounds | $R^1$ | Mp, °C. | Yield, % | Formula (MW) |
|---|---|---|---|---|
| 6b | $CH_3$ | 91 | 74 | $C_{19}H_{19}NS$ (293.43) |
| 6c | $C_2H_5$ | 96 | 35 | $C_{20}H_{21}NS$ (307.45) |
| 6d | $C_3H_7$ | 77 | 30 | $C_{21}H_{23}NS$ (321.48) |
| 6e | $iC_3H_7$ | 91 | 70 | $C_{21}H_{23}NS$ (321.48) |

Discovery Microwave System apparatus (CEM S.r.l., Cologno al Serio, Italy) was used to perform the synthesis of compounds 4a and 6b-e. Fluka silica gel 60 (230-400 mesh) was used for column chromatography. Fluka TLC plates, silica gel 60 were used for thin layer chromatography (TLC). Fluka aluminium oxide (activity II-III, according to Brockmann) was used for chromatographic purifications. Fluka Stratocrom aluminium oxide plates with fluorescent indicator were used for TLC.

3) Preparation of Compound 3a

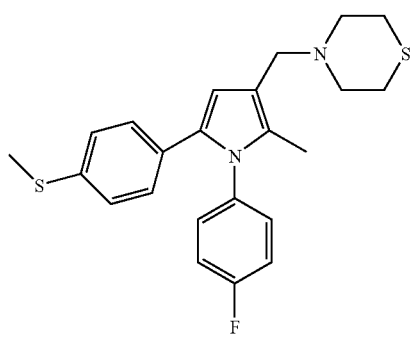

a) Thiomorpholine (0.53 g, 0.0051 mol) and formaldehyde (0.153 g, 0.0051 mol, 36.5% w/w aqueous solution) were reacted using 5.5 mL of acetic acid as the solvent.

b) Through a dropping funnel, add the obtained Mannich adduct dropwise to a solution containing compound 6a (1.51 g, 0.0051 mol) in glacial acetic acid (11.8 mL) and acetonitrile (23.5 mL).

c) Stir the mixture for 12 h at 25° C.

d) Add 30 mL of 20% w/v aqueous NaOH to neutrality.

e) Extract the mixture with ethyl acetate and wash the extracts with water to neutrality.

f) Dry the organic phase on anhydrous sodium sulphate for 2 h.

g) Purify the product by column chromatography on aluminium oxide (Brockmann, grade II-III), eluting with benzene (yield 92%).

TABLE 3

Physicochemical properties of compound 3a.

| Compd | Mp, °C. | Yield, % | Formula (MW) |
|---|---|---|---|
| 3a | 135 | 92 | $C_{23}H_{25}N_2FS_2$ (412.59) |

Spectroscopic data for compounds 3a. $^1$H NMR (CDCl$_3$): 7.27-7.25 (m, 4H), 7.16 (m, 2H), 7.01-6.97 (m, 2H), 6.27 (s, 1H), 3.46 (s, 2H), 2.78 (s broad, 4H), 2.71 (s broad, 4H), 2.51 (s, 3H), 2.04 (m, 3H).

3') Preparation of Compound 3b-h

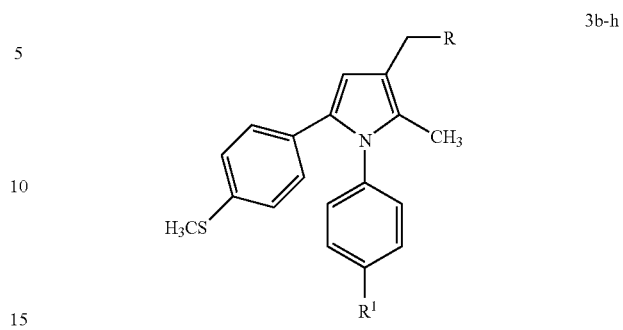

wherein
R is morpholinyl, thiomorpholinyl, N-methylpiperazinyl, piperidyl
$R^1$ is methyl, ethyl, propyl, i-propyl, fluoro.

a) Suitable amine (morpholine, thiomorpholine, N-methylpiperazine, piperidine) (0.00192 mol) and formaldehyde (0.0576 g, 0.00192 mol, 36.5% w/w aqueous solution) were reacted using 2 mL of glacial acetic acid as solvent;

b) through a dropping funnel, add the obtained Mannich adduct dropwise to a solution containing appropriate compounds 6b-e (0.00192 mol) in glacial acetic acid (4.44 mL) and acetonitrile (8.85 mL).

c) stir the mixture for 12 h at rt;

d) add 30 mL of 20% w/v aqueous NaOH to neutrality;

e) extract the mixture with ethyl acetate and wash the extracts with water to neutrality;

f) dry the organic phase on anhydrous sodium sulphate for 2 h;

g) purify the so obtained product by column chromatography on silica gel, eluting with a mixture of petroleum ether:ethyl acetate (3:1, v/v) as eluant.

TABLE 3'

Physicochemical properties of compound 3b-h.

| Compd | R | $R^1$ | Mp, °C. | Yield, % | Formula (MW) |
|---|---|---|---|---|---|
| 3b | Thiomorpholinyl | $CH_3$ | 162 | 40 | $C_{24}H_{28}N_2S_2$ (408.62) |
| 3c | Thiomorpholinyl | $C_2H_5$ | 95 | 30 | $C_{25}H_{30}N_2S_2$ (422.65) |
| 3d | Thiomorpholinyl | $C_3H_7$ | oil | 50 | $C_{26}H_{32}N_2S_2$ (436.68) |
| 3e | Thiomorpholinyl | $iC_3H_7$ | oil | 55 | $C_{26}H_{32}N_2S_2$ (436.68) |
| 3f | N-methylpiperazinyl | F | 118 | 70 | $C_{24}H_{28}N_3SF$ (409.56) |
| 3g | Piperidyl | F | 120 | 60 | $C_{24}H_{27}N_2SF$ (394.55) |
| 3h | Morpholinyl | F | 148 | 20 | $C_{23}H_{25}N_2SOF$ (396.52) |

Spectroscopic data for compounds 3b. $^1$H NMR (CDCl$_3$): 7.17 (m, 2H), 7.02 (m, 4H), 6.96 (m, 2H), 6.30 (s, 1H), 3.46 (s, 2H), 2.77 (s broad, 4H), 2.70 (s broad, 4H), 2.43 (s, 3H), 2.41 (s, 3H), 2.04 (s, 3H).

Spectroscopic data for compounds 3c. $^1$H NMR (CDCl$_3$): 7.19 (m, 2H), 7.02 (m, 4H), 6.97 (m, 2H), 6.31 (s, 1H), 3.47 (s, 2H), 2.79 (s broad, 4H), 2.69 (m, 6H), 2.41 (s, 3H), 2.05 (s, 3H), 1.28 (t, 3H).

Spectroscopic data for compounds 3d. $^1$H NMR (CDCl$_3$): 7.08 (m, 2H), 6.99 (m, 4H), 6.47 (m, 2H), 6.31 (s, 1H), 3.46 (s, 2H), 2.79 (s broad, 4H), 2.69 (s broad, 4H), 2.41 (t, 2H), 2.10 (s, 3H), 2.05 (s, 3H), 1.56 (m, 2H), 0.95 (t, 3H).

Spectroscopic data for compounds 3e. $^1$H NMR (CDCl$_3$): 7.21 (m, 2H), 7.05 (m, 2H), 7.01 (m, 2H), 6.99 (m, 2H), 6.31 (s, 1H), 3.47 (s, 2H), 2.93 (m, 1H), 2.78 (s broad, 4H), 2.72 (s broad, 4H), 2.41 (s, 3H), 2.05 (s, 3H), 1.27 (d, 6H).

Spectroscopic data for compounds 3f. $^1$H NMR (CDCl$_3$): 7.03 (m, 6H), 7.00 (m, 2H), 6.33 (s, 1H), 3.43 (s, 2H), 2.27 (s broad, 8H), 2.41 (s, 3H), 2.06 (s, 3H).

Spectroscopic data for compounds 3g. $^1$H NMR (CDCl$_3$): 7.11 (m, 2H) 7.07 (m, 4H), 7.03 (m, 2H), 6.38 (s, 1H), 3.59 (s, 2H), 2.65 (s broad, 4H), 2.44 (s, 3H), 2.10 (s, 3H), 1.83 (s broad, 4H), 1.78 (m, 2H).

Spectroscopic data for compounds 3h. $^1$H NMR (CDCl$_3$): 7.06 (m, 6H), 7.01 (m, 2H), 6.33 (s, 1H), 3.75 (s broad, 4H), 3.45 (s, 2H), 2.54 (s broad, 4H), 2.41 (s, 3H), 2.06 (s, 3H).

The NMR spectra were recorded with a Brucker AC 400 (MHz) spectrometer employing deuterochloroform (CDCl$_3$) as the solvent. Tetramethylsilane (TMS) was used as an internal standard. Melting points were determined with a Fisher-Jones apparatus and are uncorrected.

Microbiological Activity

Compounds 3a-h were dissolved in DMSO for microbiological assays.

a) Antimycobacterial Activity

Compounds 3a-h were preliminarily assayed against two freshly isolated clinical strains, M. fortuitum CA10 and M. tuberculosis B814, according to the dilution method in agar (Hawkins et al., 1991).

Growth media were Mueller-Hinton (Difco) containing 10% of OADC (oleic acid, albumine and dextrose complex) for M. fortuitum and Middlebrook 7H11 agar (Difco) with 10% of OADC for M. tuberculosis. Substances were tested at the single dose of 100 µg/mL. The active compounds were then assayed for inhibitory activity against a variety of mycobacterium strains in Middlebrok 7H11 agar by a standard twofold agar dilution method. The mycobacterium species used for biological tests were M. tuberculosis 10347, M. tuberculosis H37Rv, M. tuberculosis INH-R ATCC, M. tuberculosis RMP-R ATCC and, among atypical mycobacteria, M. smegmatis 103599, M. marinum 6423 and M. avium 103317 (from the Institute Pasteur collection). Plates were incubated at 37° C. for 3 or 28 days. BM212, INH, SM and RIF were used as reference compounds. After cultivation, MICs were read as minimal concentrations of drugs completely inhibiting visible growth of mycobacteria.

b) Inhibitory Activity on Intramacrophagic Mycobacteria.

The murine macrophage-like cell line J774.A1 was maintained in Dulbecco's modified Eagle's medium supplemented with 10% foetal calf serum (FCS). Cells were plated at density of $0.5\times10^6$ cells per well in 24-well plates and overlaid with a M. tuberculosis suspension adjusted to yield a multiplicity of infection of 20 bacteria per macrophage. Cells were then treated with the tested compound and lysed after 3 and 7 days of incubation by addition of 0.25% sodium lauryl sulphate in PBS. Lysates were neutralized by the addition of 15% bovine serum albumin in saline and aliquots of 10-fold dilutions were plated onto 7H10 agar. CFU of M. tuberculosis were counted after 28 days incubation at 37° C.

c) Cytotoxic Activity Assay

The cytotoxicity was evaluated on Vero cells grown and maintained in RPMI 1640 medium supplemented with 2 mM L-glutamine and 10% FCS. Cells were seeded in 96-well plates at a density of $1\times10^4$ cells/well. After 24 h, medium was replaced with fresh medium containing decreasing concentrations of the tested compounds and incubated at 37° C. in 5% CO$_2$. Cells were observed for morphological changes at 24, 48 and 72 of incubation. After 72 h the effects on the proliferation of Vero cells were determined by a tetrazolium-based colorimetric MTT assay. The 50% cell-inhibitory concentration (CC$_{50}$) reduced by 50% the optical density values (OD$_{540, 690}$) with respect to control no-drug treated cells.

d) Protection Index

Protection Index (PI) is the CC$_{50}$/MIC ratio (considering M. tuberculosis H37Rv).

Results

The microbiological results relative to the tests against extracellular M. tuberculosis and atypical Mycobacteria, as well as the PI, the cytotoxicity, the activity against intracellular M. tuberculosis and strains resistant to INH and RIF are reported in Tables 4-6. The inhibitory activity toward extracellular M. tuberculosis accounts for the ability of tested compounds to treat active tuberculosis. Differently, assays on intracellular M. tuberculosis assess the ability of tested compounds to inhibit mycobacteria during the latent phase of tuberculosis, before latent tuberculosis infection itself progresses to active disease. The compounds can be usefully employed in medical care. For example, compound 3a is characterized by a very interesting biological profile (Table 4).

TABLE 4

Antimycobacterial activity toward M. tuberculosis H37Rv, M. tuberculosis 103471, M. tuberculosis INH-R, M. tuberculosis RMP-R, cytotoxicity and protection index of BM212, 3a and reference compounds (INH, SM, RIF).

| Comp. | M. tuberculosis H37Rv MIC (µg/mL) | M. tuberculosis 103471 MIC (µg/mL) | M. tuberculosis INH-R MIC (µg/mL) | M. tuberculosis RMP-R MIC (µg/mL) | CC$_{50}$ (µg/mL) VERO cells | Protection Index (PI) CC$_{50}$/MIC |
|---|---|---|---|---|---|---|
| BM 212 | ND | 0.7 | ND | ND | 4 | 5.7 |
| 3a | 0.125 | <0.125 | >16 | 0.25 | >128 | >1024 |
| Isoniazid, INH | 0.25 | 0.125 | >64 | 0.25 | 32 | 128 |
| Streptomycin, SM | 0.5 | 0.3 | 0.5 | 0.5 | 64 | 128 |
| Rifampicin, RIF | 0.8 | 0.25 | 0.8 | >64 | >64 | >80 |

The activity of 3a against *M. tuberculosis* 103471 (<0.125 µg/mL) is better than those shown by INH (0.125 µg/mL), SM (0.30 µg/mL) and RIF (0.25 µg/mL), as well as better than that of the parent compound BM212 (0.70 µg/mL). Moreover, the activity of 3a toward *M. tuberculosis* H37Rv is maintained at 0.125 µg/mL, better than that of all the reference compounds.

In addition, 3a shows a very good protection index (PI=>1024) which is much higher than that found for INH and SM (PI=128) and RIF (PI=213). Therefore this compound is much less toxic than both the parent and reference compounds.

Compound 3a was also tested against resistant mycobacteria (namely, Isoniazid-resistant (INH-R), and rifampicin-resistant (RMP-R) and it is characterized by a very good antimycobacterial activity toward the RIF-R strain (0.25 µg/mL), while it is inactive (>16 µg/mL) toward the INH-R mycobacteria (Table 4).

The compound 3a was also tested toward atypical mycobacteria and the results are reported in Table 5.

TABLE 5

Antimycobacterial activity toward *M. avium*, *M. marinum* and *M. smegmatis* of BM212, 3a and reference compounds (INH, SM, RIF).

| Comp. | *M. avium* 103317 MIC (µg/mL) | *M. marinum* 6423 MIC (µg/mL) | *M. smegmatis* 103599 MIC (µg/mL) |
|---|---|---|---|
| BM 212 | 0.4 | 100 | 25 |
| 3a | 8 | 8 | 16 |
| Isoniazid, INH | 32 | 16 | 64 |
| Streptomycin, SM | 8 | 32 | 8 |
| Rifampicin, RIF | 0.3 | 0.6 | 32 |

Compound 3a shows activity toward atypical mycobacteria however at higher doses (8-16 µg/mL) than for *M. tuberculosis*, suggesting a selectivity toward *M. tuberculosis* with respect to atypical mycobacteria.

Intracellular antimycobacterial activity of BM 212, 3a and Rifampicin against intracellular *M. tuberculosis* was also assessed and the results reported in Table 6.

TABLE 6

Intracellular antimycobacterial activity of compounds BM 212, 3a and Rifampicin against intracellular *M. tuberculosis*.

| Compound | Concentration [µg/ml] | | | |
|---|---|---|---|---|
| | 1 | 0.5 | 0.25 | 0.125 |
| BM212 | 51.76 | 32.35 | 29.41 | 0 |
| 3a | 99.81 | 99.72 | 99.02 | 96.12 |
| Rifampicin | 99.97 | 99.93 | 99.83 | 96.59 |

Data are expressed as % of growth reduction respect to untreated controls after 6 days of treatment.

3a exerts a bactericidal activity on intracellular mycobacteria. The activity of 3a against intracellular *M. tuberculosis* was determined at several concentrations using the J774.A1 murine macrophage cell line infected with *M. tuberculosis* H37Rv. At the concentration of 0.125 µg/mL a 96.12% reduction of mycobacterial survival was observed with compound 3a, comparable to the reduction induced by rifampicin at same concentration and much higher than the reduction observed with BM 212 at the same concentration.

It has been shown that mycobacteria can reside for years inside lymphoid cells and macrophages as latent tuberculosis. It is also known that combating latent tuberculosis infection is one of the major challenges for reducing the high rate of progression to active disease in immuno-compromised individuals. Many traditional drugs are unable to target such latent mycobacteria. By contrast, the compound 3a is very active against intracellular mycobacteria, thus being a good candidate for treating latent tuberculosis.

All the experimental evidences reported in the present invention (low cyto-toxicity, activity against resistant strains of *M. tuberculosis*, activity against latent tuberculosis) make compound 3a an extremely interesting therapeutic compound when compared to the currently therapies. For instance, current drugs are poorly active or inactive against drug-resistant mycobacteria, therefore, a multi-drug therapy is needed.

In this context and considering the reduced toxicity of the pyrrole derivatives of the present invention, it is suggested that they may be used alone or in combination with other anti-tubercular compounds for the treatment of tuberculosis.

The microbiological results of compounds 3b-h relative to the tests against *M. tuberculosis* and atypical Mycobacteria, as well as the PI, the cytotoxicity and activity against strains resistant to INH and RIF are reported in Tables 7-9. The inhibitory activity toward *M. tuberculosis* accounts for the ability of tested compounds to treat active tuberculosis. The compounds can be usefully employed in medical care. Compounds 3b-h are characterized by a very interesting biological profile even though they are less active than 3a, but more active than reference compounds with the exception of compounds 3f-g.

TABLE 7

Antimycobacterial activity toward *M. tuberculosis* H37Rv, *M. tuberculosis* 103471, *M. avium* of 3b-h, BM212, 3a and reference compounds (INH, SM, RIF).

| Compd | R | R$^1$ | *M. tuberculosis* H37Rv MIC (µg/mL) | *M. tuberculosis* 103471 MIC (µg/mL) | *M. avium* 103471 MIC (µg/mL) |
|---|---|---|---|---|---|
| 4a | Thiomorpholinyl | CH$_3$ | 0.25 | 0.25 | 16 |
| 4b | Thiomorpholinyl | C$_2$H$_5$ | 0.25 | 0.25 | >16 |
| 4c | Thiomorpholinyl | C$_3$H$_7$ | 0.5 | 0.125 | 8 |
| 4d | Thiomorpholinyl | iC$_3$H$_7$ | 0.5 | 0.125 | 8 |
| 4e | N-methylpiperazinyl | F | 2 | 2 | 4 |

TABLE 7-continued

Antimycobacterial activity toward *M. tuberculosis* H37Rv, *M. tuberculosis* 103471, *M. avium* of 3b-h, BM212, 3a and reference compounds (INH, SM, RIF).

| Compd | R | R$^1$ | *M. tuberculosis* H37Rv MIC (μg/mL) | *M. tuberculosis* 103471 MIC (μg/mL) | *M. avium* 103471 MIC (μg/mL) |
|---|---|---|---|---|---|
| 4f | Piperidyl | F | NS | 8 | NS |
| 4g | Morpholinyl | F | 0.5 | 0.25 | 16 |
| BM 212 | | | ND | 0.7 | 0.4 |
| Isoniazid, INH | | | 0.25 | 0.125 | 32 |
| Streptomycin, SM | | | 0.5 | 0.3 | 8 |
| Rifampicin, RIF | | | 0.8 | 0.25 | 0.3 |
| 3a | Thiomorpholinyl | F | 0.125 | <0.125 | 8 |

TABLE 8

Antimycobacterial activity toward *M. tuberculosis* Rif-R, *M. tuberculosis* INH-R, *M. tuberculosis* PZA-R, *M. tuberculosis* SM-R of 3b-h, BM212, 3a and reference compounds (INH, SM, RIF).

| Compd | R | R$^1$ | Rif-R$^a$ MIC (μg/mL) | INH-R$^b$ MIC (μg/mL) | PZA-R$^c$ MIC (μg/mL) | SM-R$^d$ MIC (μg/mL) |
|---|---|---|---|---|---|---|
| 3b | Thiomorpholinyl | CH$_3$ | 0.25 | 16 | 0.5 | 0.25 |
| 3c | Thiomorpholinyl | C$_2$H$_5$ | 0.25 | 16 | 0.25 | 0.25 |
| 3d | Thiomorpholinyl | C$_3$H$_7$ | 0.5 | 8 | 0.5 | 0.25 |
| 3e | Thiomorpholinyl | iC$_3$H$_7$ | 1 | 16 | 1 | 0.125 |
| 3f | N-methylpiperazinyl | F | 2 | 8 | 2 | 1 |
| 3g | Piperidyl | F | NS | NS | NS | NS |
| 3h | Morpholinyl | F | 2 | >16 | 0.5 | 0.25 |
| BM 212 | | | ND | ND | ND | ND |
| Isoniazid, INH | | | 0.25 | >64 | — | — |
| Streptomycin, SM | | | 0.5 | 0.5 | — | — |
| Rifampicin, RIF | | | >64 | 0.8 | — | — |
| 3a | Thiomorpholinyl | F | 0.25 | >16 | — | — |

$^a$Rif-R: Rifampicin-resistant mycobacteria;
$^b$INH-R: isoniazide-resistant mycobacteria;
$^c$PZA-R: pirazinamide-resistant mycobacteria;
$^d$SM-R: streptomycin-resistant mycobacteria;

TABLE 9

Cytotoxicity and Protection Index (PI) of 3b-h, BM212, 3a and reference compounds (INH, SM, RIF).

| Compd | R | R$^1$ | CC$_{50}$ (μg/mL) VERO cells | Protection Index (PI) CC$_{50}$/MIC |
|---|---|---|---|---|
| 3b | Thiomorpholinyl | CH$_3$ | 18.40 | 73.6 |
| 3c | Thiomorpholinyl | C$_2$H$_5$ | 17.18 | 68.72 |
| 3d | Thiomorpholinyl | C$_3$H$_7$ | 25.25 | 202 |
| 3e | Thiomorpholinyl | iC$_3$H$_7$ | 37.58 | 300.64 |
| 3f | N-methylpipiperazinyl | F | 9.33 | 4.66 |
| 3g | Piperidyl | F | ND | ND |
| 3h | Morpholinyl | F | 44.34 | 177.52 |
| BM 212 | | | 4 | 5.7 |
| Isoniazid, INH | | | 32 | 128 |
| Streptomycin, SM | | | 64 | 128 |
| Rifampicin, RIF | | | >64 | >80 |
| 3a | Thiomorpholinyl | F | >128 | >1024 |

The activities of compounds 3b-e,h against *M. tuberculosis* 103471 are in general comparable or better than those shown by INH (0.125 μg/mL), SM (0.30 μg/mL) and RIF (0.25 μg/mL), as well as better than that of the parent compound BM212 (0.70 μg/mL) and comparable to that of parent compound 3a (0.125 μg/mL). Moreover, the activities of 3b-e,h toward *M. tuberculosis* H37Rv are comparable or, sometimes, better than those of the reference compounds (Table 7).

In addition, compounds 3b-h show a very good protection index that, in any case, is lower than those of all the reference compounds. Thus the compounds of the present invention display a lower cytotoxicity (Table 9).

Compounds 3b-h were also tested against resistant mycobacteria (namely, Isoniazid-resistant (INH-R), Rifampicin-resistant (RMP-R) and Pirazinamid-resistant (PZA-resistant). Compounds 3b-e are in general characterized by a very good antimycobacterial activity toward the RIF-R, PZA-R and SM-R strains (range 0.25-0.5 μg/mL), while they are characterized by a very low activity toward the INH-R mycobacteria (8-16 μg/mL) (Table 4). Compound 3h was characterized by a very good antimycobacterial activity toward the PZA-R and SM-R strains (0.5 and 0.25 μg/mL, respectively).

The compounds 3b-h were also tested toward *M. avium* and the results are reported in Table 4. Compounds 3b-h show activity toward *M. avium* however at higher doses (4→16 μg/mL) than for *M. tuberculosis*, suggesting selectivity toward *M. tuberculosis* with respect to *M. avium*.

BIBLIOGRAPHY

Duncan, K. et al. *Curr. Opin. Microbiol.* 7, 460-465, 2004
Deidda, D. et al, *Antimicrob. Agents Chemother.* 42, 3035-3037, 1998
Biava M., et al *Bioorg. Med. Chem. Lett.* 9, 2983-2988, 1999
Biava M., et al *Med. Chem. Res.* 9, 19-34, 1999b
Biava M., et al *Bioorg. Med. Chem.* 11, 515-520, 2003
Biava M., et al *Bioorg. Med. Chem.* 12, 1453-1458, 2004
Biava M., et al *Bioorg. Med. Chem.* 13, 1221-1230, 2005
Biava M., et al *J. Med. Chem.* 49, 4946-4952, 2006
Hawkins, J. E.; Wallace Jr., R. J.; Brown, A.; 1991, Antibacterial susceptibility test: Mycobacteria: in A. Balows, W. J.

Hausler Jr., K. L. Hermann, H. D. Isenberg, H. J. Shadomy (eds.). Manual of Clinical Microbiology, 5th edn., American Society for Microbiology, Washington, D.C.

World Health Organization. 2006 Tuberculosis Facts. http://www.who.int/mediacentre/factsheets/fs104/en/

The invention claimed is:

1. A compound having the general formula 3

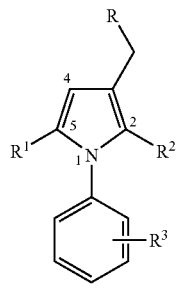

wherein:

R represents a morpholinyl, oxane, thioxane, piperidyl or imidazolyl group;

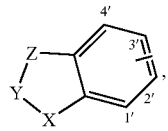

$R^1$ is when Z is not present, $R^1$ is a substituted phenyl ring selected from: a o-, p- or m-methylsulfanyl phenyl, (Y=methyl, X=S), a o-, p- or m-ethylsulfanyl phenyl (Y=ethyl, X=S), a o-, p- or m-propylsulfanyl phenyl (Y=propyl, X=S), a o-, p- or m-isopropylsulfanyl phenyl (Y=isopropyl, X=S), a o-, p- or m-butylsulfanyl phenyl (Y=butyl, X=S), a o-, p- or m-isobutylsulfanyl phenyl (Y=isobutyl, X=S), a o-, p- or m-cyclopentylsulfanyl phenyl (Y=cyclopentylsulfanyl, X=S), a o-, p- or m-cyclohexylsulfanyl phenyl (Y=cyclohexyl, X=S), a o-, p- or m-methylsulfinyl phenyl (Y=methyl, X=SO), a o-, p- or m-methylsulfonyl phenyl (Y=methyl, X=SO$_2$), a o-, p- or m-sulfamoyl phenyl (Y=NH$_2$, X=SO$_2$), a o-, p- or m-methylsulfamoyl phenyl (Y=NHCH$_3$, X=SO$_2$) or a o-, p- or m-dimethylsulfamoyl phenyl (Y=N(CH$_3$)$_2$, X=SO$_2$) group;

$R^1$ is also a fused 5-6 heterocyclic ring represented by a benzo[b]thiophene (X=S, Y=Z=CH), benzo[c]thiophene (Y=S, X=Z=CH), benzo-1,2-thiazole (X=S, Y=N, Z=CH), and benzo-1,3-thiazole (X=S, Y=CH, Z=N) wherein the benzo[b]thiophene, the benzo-1,2-thiazole, and the benzo-1,3-thiazole can be bound to the C5 of the pyrrole ring through the carbon atom C1', C2', C3', or C4' and the benzo[c]thiophene can be bound to the C5 of the pyrrole ring through the carbon atom C1' or C2';

$R^2$ is H, methyl, ethyl, isopropyl, benzyl, o-chlorobenzyl, m-chlorobenzyl, p-chlorobenzyl, o-fluorobenzyl, m-fluorobenzyl, p-fluorobenzyl, o-methylbenzyl, m-methylbenzyl, p-methylbenzyl, o-trifluorobenzyl, m-trifluorobenzyl, p-trifluorobenzyl, o-methoxybenzyl, m-methoxybenzyl or p-methoxybenzyl;

$R^3$ is o-methyl, m-methyl, p-methyl, o-ethyl, m-ethyl, p-ethyl, o-propyl, m-propyl p-propyl, o-isopropyl, m-isopropyl, p-isopropyl, o-methoxy, m-methoxy, p-methoxy, o-trifluoromethyl, m-trifluoromethyl, p-trifluoromethyl, o-chloro, m-chloro, p-chloro, o, o-dichloro, m-dichloro, o,p-dichloro, o-fluoro, m-fluoro, p-fluoro, o,o-difluoro, m,m-difluoro, o,p-difluoro, 1-naphthyl, o-methylsulfanyl, m-methylsulfanyl, p-methylsulfanyl, o-ethylsulfanyl, m-ethylsulfanyl, p-ethylsulfanyl, o-propylsulfanyl, m-propylsulfanyl, p-propylsulfanyl, o-isopropylsulfanyl, m-isopropylsulfanyl, p-isopropylsulfanyl, o-butylsulfanyl, m-butylsulfanyl, p-butylsulfanyl, o-isobutylsulfanyl, m-isobutylsulfanyl, p-isobutylsulfanyl, o-cyclopentylsulfanyl, m-cyclopentylsulfanyl, p-cyclopentylsulfanyl, o-cyclohexylsulfanyl, m-cyclohexylsulfanyl, p-cyclohexylsulfanyl, o-SOMe, m-SOMe, p-SOMe, o-SO$_2$Me, m-SO$_2$Me, p-SO$_2$Me, o-SO$_2$NH$_2$, m-SO$_2$NH$_2$, p-SO$_2$NH$_2$, o-SO$_2$NHMe, m-SO$_2$NHMe, p-SO$_2$NHMe, o-SO$_2$NMe$_2$, m-SO$_2$NMe$_2$ or p-SO$_2$NMe$_2$.

2. A pharmaceutical composition comprising the compound according to claim 1, and appropriate excipients and diluents.

3. The pharmaceutical composition according to claim 2 further comprising at least another compound endowed with antitubercular activity selected from the group consisting of isoniazid, rifampicin, pyrazinamide, ethambutol, streptomycin, cycloserin and para-aminosalicylic acid.

4. Process for the preparation of a compound according to claim 1 comprising the following steps:

a) reacting methyl vinyl ketone with a suitable aryl aldehyde having the following formula 5

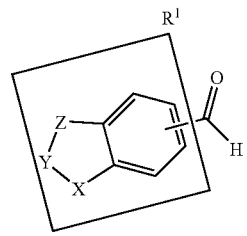

wherein $R^1$ is defined as in claim 1;

in the presence of 3-ethyl-5-(2-hydroxyethyl)-4-methylthiazolium bromide and triethylamine under conditions suitable for obtaining the appropriate intermediate 4

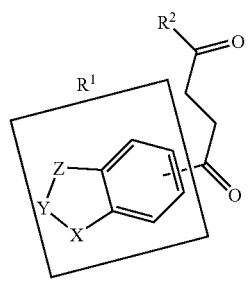

wherein $R^1$ and $R^2$ are defined as in claim 1;

b) extracting and/or purifying compound 4 as obtained under a);

c) reacting compound 4 with appropriate aniline 7

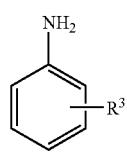

wherein $R^3$ is defined as in claim 1;

under conditions suitable for obtaining the appropriate intermediate 6;

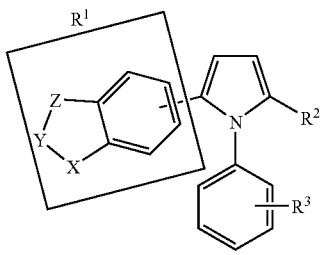

6 wherein $R^1$, $R^2$ and $R^3$ are defined as in claim 1;

d) purifying compound 6 as obtained under c);

e) allowing an amine selected from the group consisting of morpholine, piperidine, and imidazole to react with formaldehyde adding compound 6 under conditions suitable for obtaining the appropriate compound 3;

f) extracting and/or purifying product 3 as obtained under e).

5. A method of treating tuberculosis, comprising administering a compound of claim 1 to a patient in need thereof.

* * * * *